United States Patent [19]

Christmann et al.

[11] 4,020,120

[45] Apr. 26, 1977

[54] MODIFIED ZINC FERRITE OXIDATIVE DEHYDROGENATION CATALYSTS

[75] Inventors: Harold F. Christmann, Seabrook; Edward J. Miklas, Conroe, both of Tex.

[73] Assignee: Petro-Tex Chemical Corporation, Houston, Tex.

[22] Filed: Dec. 8, 1975

[21] Appl. No.: 638,742

Related U.S. Application Data

[62] Division of Ser. No. 502,382, Sept. 3, 1974, Pat. No. 3,998,760.
[52] U.S. Cl. ..................... 260/680 D; 260/680 E
[51] Int. Cl.$^2$ ........................................ C07C 11/12
[58] Field of Search ................. 260/680 E, 680 D; 252/471, 473, 475

[56] References Cited

UNITED STATES PATENTS

| | | | |
|---|---|---|---|
| 3,849,545 | 11/1974 | Miklas | 260/680 E |
| 3,900,525 | 8/1975 | Christmann et al. | 260/680 E |
| 3,925,498 | 12/1975 | Stadig | 260/680 E |
| 3,937,746 | 2/1976 | Croce et al. | 260/680 E |
| 3,937,748 | 2/1976 | Miklas | 260/680 E |

*Primary Examiner*—Oscar R. Vertiz
*Assistant Examiner*—Wayne A. Langel
*Attorney, Agent, or Firm*—Kenneth H. Johnson; N. Elton Dry

[57] ABSTRACT

Improved oxidative dehydrogenation catalysts are prepared by modifying a zinc ferrite oxidative dehydrogenation catalyst with magnesium oxide. The resulting catalyst compositions exhibit higher conversions and yields.

8 Claims, No Drawings

MODIFIED ZINC FERRITE OXIDATIVE DEHYDROGENATION CATALYSTS

This is a division of application Ser. No. 502,382, filed Sept. 3, 1974, Pat. No. 3,998,760.

BACKGROUND OF THE INVENTION

1. Field of the Invention

This invention relates to a process for dehydrogenating hydrcarbons. More particularly, this invention relates to the oxidative dehydrogenation of organic compounds in the presence of modified zinc ferrite catalyst compositions.

2. Description of the Prior Art.

Oxidative dehydrogenation processes wherein zinc ferrite catalyst compositions have been employed to convert saturated and/or unsaturated hydrocarbons to more highly unsaturated hydrocarbons through removal of hydrogen from such hydrocarbons are known in the art. See, for example, U.S. Pat. No. 3,303,235. However, such catalyst compositions do not retain their good initial activity and deteriorate rapidly under the reaction conditions of the oxidative dehydrogenation process. Such deterioration necessitates the frequent and uneconomic regeneration of the catalyst composition.

Accordingly, it is an object of the present invention to provide cataylst composition which, when employed in oxidative dehydrogenation processes, effect high conversions at high selectivities to the desired product.

It is another object of the present invention to provide more stable and, hence, longer-lived catalyst compositions than heretofore employed in oxidative dehydrogenation processes.

SUMMARY OF THE INVENTION

In accordance with the present invention, a process is provided for the oxidative dehydrogenation of organic compounds which comprises contacting an organic compound having from about 2 to about 20 carbon atoms and oxygen in the presence of a zinc ferrite catalyst composition additionally containing magnesium oxide as a catalyst modifier, in an amount of from about 0.1 to about 10 wt. % baseed on the weight of the zinc ferrite composition.

DESCRIPTION OF THE PREFERRED EMBODIMENTS

In accordance with the process of the instant invention, certain organic compounds are dehydrogenated to less saturated compounds of the same carbon number at elevated temperature in the presence of oxygen and the catalysts of the instant invention.

The process of this invention may be applied to the dehydrogenation of a wide variety of organic compounds. Such compounds normally will contain from 2 to 20 carbon atoms, at least one

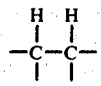

grouping, a boiling point below about 350° C., and such compounds may contain other elements, in addition to carbon and hydrogen such as oxygen, halogens, nitrogen and sulfur.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustrative dehydrogenations which may be carried out by the process of this invention include propionitrile to acrylonitrile; propionaldehyde to acrolein; ethylchloride to vinyl chloride; methyl isobutyrate to methyl metacrylate; 2 or 3 chlorobutene-1 or 2,3-dichlorobutane to chlorprene; ethyl pyridine to vinyl pyridine; ethylbenzene to styrene; isopropylbenzene to α-methyl styrene; ethylcyclohexane to styrene; cylohexane to benzene; ethane to ethylene or acetylene; propane to propylene, methylacetylene, allene, or benzene; isobutane to isobutylene; n-butane to butene and butadiene; n-butene to butadiene-1,3 and vinyl acetylene; methyl butene to isoprene; cyclopentane to cyclopentene and cyclopentadiene-1,3; n-octane to ethyl benzene and orthoxylene, monomethylheptanes to xylenes; ethyl acetate to vinyl acetate; methyl isobutyrate to methyl methacrylate; 2,4,4-trimethylpentane to xylenes; and the like. Other materials which are dehydrogenated by the process of this invention include ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1,3-dichlorobutane, 1,4-dichlorobutane, the chlorofluoroethanes, methyl pentane, methylethyl ketone, diethyl ketone, n-butyl alcohol, methyl propionate, and the like.

The catalyst compositions of this invention are also useful for the formation of new carbon-to-carbon bonds by the removal of hydrogen atoms. For example, acyclic compounds having from 6 to about 16 carbon atoms and no quaternary carbon atoms are converted to cyclic compounds of greater degree of unsaturation, e.g., n-hexene to benzene. Also, propene is converted to diallyl.

The preferred compounds which are dehydrogenated by the process of this invention are hydrocarbons having from about 3 to about 12 carbon atoms, including alkanes, alkenes, cycloalkanes, cycloalkenes, and aromatic compounds having one or two alkyl side chains of from 2 to 3 carbon atoms. A preferred hydrocarbon feed for the process of this invention would be selected from the group of n-butane, n-butene, pentane or pentene including all isomers and mixtures thereof, the methyl butenes, the hexenes, ethyl benzene, etc. and mixtures thereof. Especially preferred are acyclic hydrocarbons having 4 to 5 contiguous non-quaternary carbon atoms, such as butane, the butenes, the methyl butenes and mixtures thereof.

In the instant process, the organic compound is dehydrogenated in the presence of oxygen. Oxygen may be fed to the reaction zone as pure oxygen, air, oxygen-enriched air, oxygen mixed with a diluent, and so forth. Oxygen in the desired amount may be added in the feed to the dehydrogenation zone and oxygen may also be added in increments to the dehydrogenation zone. The oxygen may be supplied in a cyclic manner such as described in U.S. Pat. No. 3,420,911.

The amount of oxygen employed in the oxidative dehydrogenation process will vary depending upon the particular compound being dehydrogenerated, the number of hydrogen atoms being removed, and the conversion level. For example, in dehydrogenating butane to butene, less oxygen is generally employed than if the reaction were carried out to produce butadiene. Normally oxygen will be supplied in the dehydrogenation zone in an amount from about 0.2 to about 1.5, and preferably from about 0.3 to about 1.2 mols of oxygen per mol of $H_2$ being liberated from the organic compound. Expressed in terms of the organic compound being dehydrogenated, the oxygen is supplied in an amount of from about 0.2 to 2.0 mols per mol of organic compound to be dehydrogenated with a preferred range of from about 0.25 to 1.5 mols of oxygen per mol of organic compound.

Preferably, the reaction mixture contains a quantity of steam or a diluent such as nitrogen. These gases serve to reduce the partial pressure of the organic compound, however, the functions of steam in the reaction are several fold in that the steam does not act merely as a diluent. Whenever steam is employed in the process of the instant invention, it is employed in an amount generally of from about 2 to about 40 mols of steam per mol of organic compound to be dehydrogenated, with an amount of from about 3 to about 35 mols of steam per mol of organic compound to be hydrogenated being preferred. Especially preferred are amounts of from about 5 to about 30 mols of steam per mol of organic compound to be dehydrogenated. Whenever a diluent is employed instead of steam, such diluents generally may be used in the same quantites as specified for steam.

In one modification of this invention, halogen is present in the reaction gases. The presence of halogen in the dehydrogenation zone is particularly effective whenever the compound to be dehydrogenated is a saturated hydrocarbon. Whenever halogen is employed in the dehydrogenation zone, it is provided as elemental halogen or a compound of halogen which liberates halogen under the conditions of the dehydrogenation reaction. Suitable sources of halogen include hydrogen iodide, hydrogen bromide and hydrogen chloride; aliphatic halides such as ethyl iodide, methyl bromide, methyl chloride, and 1,2-dibromoethane; cycloaliphatic halides; ammonium iodide, ammionium bromide, ammonium chloride, sulfuryl chloride; metal halides including moten halides; and the like. The halogen also may be liberated partially or entirely by a solid source as disclosed in the process of U.S. Pat. No. 3,130,241 issued Apr. 21, 1964. Mixtures of various sources of halogen may be used. Whenever employed in the process of the instant invention, the amount of halogen employed (calculated as elemental halogen) is from about 0.0001 to about 1.0 mols of halogen per mol of the organic compound to be dehydrogenated with an amount of from about 0.01 to about 0.5 mols of halogen per mol of organic compound being preferred.

AThe catalyst compositions useful in the present invention include zinc ferrites containing, as the active components thereof, zinc, iron and oxygen in combination as hereinafter described and additionally containing free magnesium oxide as a modifier.

The zinc ferrite constituents of the instant catalyst compositions comprise zinc ferrite of the empirical fromula $Zn_xFe_yO_z$, wherein $x$ will be from about 0.1 to 2, inclusive, and $y$ can be in the range of about 0.3 to 12, inclusive, and $z$ will vary depending upon the number of oxygen vacancies, but will usually be within the range of about 3 to 18, inclusive. Especially preferred are zinc ferrite compositions wherein the ratio of $y$ to $x$ is from about 2:1 to about 5:1. Although the modified zinc ferrite calayst may be broadly defined as containing crystalline structures of iron, oxygen and zinc, certain types of catalysts are preferred. Zinc ferrite formation may be accomplished by reacting an active compound of iron with an active compound of zinc. By the term active compound is meant a compound which is reactive under the conditions hereinafter described to form the ferrite. The active compounds are suitably oxides or compounds which are converted to oxides during the formation of the ferrite, such as organic and inorganic salts or hydroxides. Active compounds of iron and zinc include the nitrates, hydroxides, hydrates, oxalates, carbonates, acetates, formates, halides, oxides, etc. For example, zinc carbonate may be reacted with iron oxide hydrates to form zinc ferrite. Salts of the desired metals may be co-precipitated and the precipitate heated to from the ferrite. Desired ferrites may be obtained by conducting the reacton to form the ferrite at relatively low temperatures, that is, at temperatures lower than some of the very high temperatures used for the formation of some of the semiconductor applications. Good results have been obtained by heating the ingredients to a temperature high enough to produce the zinc ferrite, but at conditions no more severe than equivalent to heating to 850° C. for 90 minutes in air. Generally, the maximum temperature will be less than 700° C. and preferably about 650° C. Methods for preparing zinc ferrite catalyst compositions suitable for use in the process of this invention are disclosed in U.S. Pat. Nos. 3,270,080: 3,284,536; 3,303,235–6; 3,303,238; 3,308,182; 3,334,152; 3,420,912; 3,440,299; 3,342,890 and 2,450,787.

As is apparent from the empirical formula presented herein for zinc ferrite, the ratio of iron to zinc in such ferrite mixtures is not restricted to the stoichiometric ratios as would be present in the simple compound zinc ferrite. In the catalyst compositions of the instant invention, there is present zinc ferrite compound as well as one or more oxides of the constituent cations. For example, if the active compounds are employed such that in the empirical formula $y$ is about 3 and $x$ is 1, the catalyst composition formed therefrom will contain iron oxide in addition to the zinc ferrite formed. Similarly, the zinc ferrite precursor composition may comprise an excess of zinc over the stoichiometric amount to form the ferrite, in which case the resulting catalyst will contain zinc oxide in addition to the zinc ferrite formed.

The preferred zinc ferrite catalyst compositions of the instant invention are those having a face centered cubic structure. However, the zinc ferrites of the instant invention will not be present in the most highly oriented crystalline structure because it has been found that superior results may be obtained with catalysts wherein the zinc ferrite is relatively disordered. Such catalyst compositions may be obtained by conducting the reaction to form the zinc ferrite at relatively low temperatures as described herein.

The zinc ferrite catalyst compositions of the present invention can be identified by their characteristic X-ray diffraction patterns. The preferred catalyst compositions will gererally have X-ray diffraction peaks at d-spacings within or about 4.83 to 4.89; 2.95 to 3.01; 2.51 to 2.57; 2.40 to 2.46; 2.08 to 2.14; 1.69 to 1.75; 1.59 to 1.65; and 1.46 to 1.52; with the most intense peak being between 2.51 to 2.57. Particularly preferred catalysts will have d-spacings within or about 4.81 to 4.88; 2.96 to 3.00; 2.52 to 2.56; 2.41 to 2.45; 2.09 to 2.13; 1.70 to 1.74; 1.60 to 1.64; and 1.47 to 1.51, with the most intense peak falling within or about 2.52 to 2.56. These X-ray determinations are suitably run with a cobalt tube.

The magnesium oxide catalyst modifier of the instant invention can be employed in the form of magnesium oxide itself or a magnesium compound which will be converted to magnesium oxide under the reaction conditions set forth herein. Particularly effective are inorganic magnesium compounds such as the oxides and salts, including the phosphates, phosphites, sulfites, thiocyanates, thiosulfates, and the like. Specially preferred are magnesium oxide and magnesium carbonate.

The magnesium oxide or magnesium oxide precursor catalyst modifier may be added to the zinc ferrite by any suitable method. The modifier may be incorporated into the catalyst precursor mixture or may be added after zinc ferrite has been formed. If a catalyst support or carrier is employed, one convenient method is to form a slurry of the modifier with the zinc ferrite prior to coating on the support. Although aqueous mediums will generally be employed when coating a support with the catalyst constituents, it is comtemplated that non-aqueous systems can also be employed, if desired, in the preparation of the catalyst. Another suitable method for incorporating the modifier into the zinc ferrite composition is by dry-mixing the components.

The magnesium oxide modifier is present in the zinc ferrite catalyst compositon in a catalytic promoting amount. Generally, a catalytic promoting amount of magnesium oxide will be not more than about 10% by weight, based on the total weight of the zinc ferrite composition present. Amounts of magnesium oxide of from about 0.1 to 10% are satisfactory, with amounts of from about 1.0 to about 5.0%, based on the weight of zinc ferrite composition being preferred.

In an even more preferred catalyst compositon according to the present invention, manganese oxide is present as a modifier in addition to mmagnesium oxide.

The manganese oxide catalyst modifier of the instant invention can be employed in the form of manganese oxide itself or manganese compound which will be converted to manganese oxide under the reaction conditions set forth herein. Particularly effective are inorganic manganese compounds such as the ozides and salts, including the phosphates sulfates, phosphites, sulfites, silicates, thiocyanates, thiosulfates, and the like. Specially preferred are manganese oxide and manganese carbonate.

The manganese oxide or manganese oxide precursor catalyst modifier may be added to the zinc ferrite by any suitable method in the same manner as the magnesium oxide or precursor.

The manganese oxide modifier is present in the zinc ferrite catalyst composition in a catalytic promoting amount. Generally, a catalytic promoting amount of manganese oxide will be not more than about 10% by weight, based on the total weight of the zinc ferrite composition present. Amounts of manganese oxide of from about 0.1 to 10% are satisfactory, with amounts of from about 1.0 to about 5.0%, based on the weight zinc ferrite composition being preferred.

Catalyst binding agents for fillers not mentioned herein may also be used, but these will not ordinarily exceed about 50 percent or 75 percent by weight of the catalytic surface, and the described catalytic compositions will preferably constitute the main active constituent. These other binding agents and fillers will preferably be essentially inert. Preferred catalysts are those that have as a catalytic surface exposed to the reaction gases at least 25 or preferably 50 weight percent of the defined catalytic surface. The catalytic surface may be introduced as such or it may be deposited on a carrier by methods known in the art such as by preparing an aqueous solution or dispersion of a catalytic material and mixing the carrier with the solution or dispersion until the active ingredients are coated on the carrier. If a carrier is utilized, very useful carriers are silicon carbide, aluminum oxide, pumice, and the like. Other known catalyst carriers may be employed. When carriers are used, the amount of catalyst on the carrier will suitably be between about 5 to 75 weight percent of the total weight of the active catalytic material plus carrier. Another method for introducing the required surface is to utilize as a reactor a small diameter tube wherein the tube wall is catalytic or is coated with catalytic material. Other methods may be utilized to introduce the catalytic surface such as by the use of rods, wires, mesh, or shreds, and the like, of catalytic material. The catalytic surface described is the surface which is exposed in the dehydrogenation zone to the reaction gases, that is, e.g., if a catalyst carrier is used, the composition described as a catalyst refers to the composition of the surface and not to the total compositon of the surface coating plus carrier.

The catalyst compositions of the instant invention may be activated prior to use by treatment with a reducing gas, such as, for example, hydrogen or hydrocarbons. For example, the reduction may be effected with hydrogen at a temperature of from about 500° to about 1,000° F., with temperatures of from about 650° to about 850° F. being preferred. The time required for reduction will be dependent upon the temperature selected for the reducing step and will generally be from about ten minutes to about two hours.

The catalyst compositions of this invention may also comprise additives, such as disclosed in U.S. Pat. No. 3,270,080 and U.S. Pat. No. 3,303,238. Phosphorus, silicon, boron, sulfur, or mixtures thereof, are examples of additives. Excellent catalyst may contain less than 5 wt.%, and preferaby less than 2 wt.%, of sodium or potassium in the catalyst composition. The catalyst compositions of this invention may also comprise other metallic promoters as are well-known in the art.

The Reaction Conditions. The temperature for the dehydrogenation reaction will depend upon the compound being dehydrogenated and the desired level of conversion. Generally, temperatures of from about 500° to about 1,200° F. are satisfactory with temperatures of from about 650° F. to about 1,100° F. being preferred.

The process of the instant invention is carried out at atmospheric pressure, superatomospheric pressure or at subatmospheric pressure. The reaction pressure will normally be about or in excess of atmospheric pressure, although subatmospheric pressure may also desirably be used. Generally, the total pressure will be between about 2 p.s.i.a. and about 125 p.s.i.a., with a total pressure of from 4 p.s.i.a. to about 75 p.s.i.a. being preferred. Excellent results are obtained at about atmospheric pressure.

The gaseous reactants may be conducted through the dehydrogenation zone at a fairly wide range of flow rates. Thee optimum flow rate will depend upon such variables as the temperature and pressure of reaction, and the particular hydrocarbon being dehydrogenated.

Desirable flow rates may be established by one skilled in the art. Generally, the flow rates will be within the range of about 0.10 to 15 liquid volumes of the organic compound to be dehydrogenated per volume of dehydrogenation zone containing catalyst per hour (referred to as LHSV). Usually, the LHSV will be between 0.15 and about 5.0.

In calculating space velocities, the volume of a fixed bed dehydrogenation zone containing catalyst is that original void volume of reactor space containg catalyst. The gaseous hourly space velocity (GHSV) is the volume of the hydrocarbon to be dehydrogenated, in the form of vapor calculated under standard conditions of 25° C. and 760 mm. of mercury, per volume of reactor space containing catalyst per hour. Generally, the GHSV will be between about 25 and 6400, and excellent results are obtained between about 38 and 3800. Suitable contact times are, for example, from about 0.001 or higher to about 5 or 10 seconds, with particularly good results being obtained between 0.01 and 3 seconds. The contact time is the calculated dwell time of the reaction mixture in the reaction zone, assuming the mols of product mixture are equivalent to the mols of feed mixture. For the purpose of calculation of residence times, the reaction zone is the portion of the reaction containing catalyst.

The process of this invention is suitably deployed with a fixed catalyst bed or a moving catalyst bed, such as a fluidized catalyst bed in the dehydrogenation zone.

The following examples are illustrative only of the invention and are not intended to limit the invention. All percentages are weight percent unless specified otherwise. All conversions, selectivities and yields are expressed in mol percent of the designated feed.

EXAMPLE I

A. Preparation of a Magnesium-Modified Zinc-Ferrite Catalyst Composition

To approximately 35 liters of distilled water were added 6,570 g. of 87% ferric oxide, 3,733 g. zinc carbonate and 51.6 g. zinc chloride to form a slurry. By emission spectra analysis, the zinc carbonate (Naftone F-5637) was shown to contain 1.0% magnesium and 49.0% zinc, as metal. This corresponds to a magnesium carbonate content of approximately 3.6 wt.% of the zinc carbonate-magnesium carbonate mixture. The slurry was thoroughly mixed for five hours after which time is was dewatered by filtering and the filter cake was dried in an oven at 260° F. for 12 hours. The dried filter cake thus obtained was granulated and blended in a Patterson-Kelly blender with enough water to form moist granules. The granules were then dried at 260° F. for 12 hours. After drying, the granules were calcined at 1,200° F. for 14 minutes in the presence of oxygen to form a zinc ferrite-magnesium oxide-containing catalyst composition. The catalyst composition was analyzed by X-ray diffraction and found to contain zinc ferrite, magnesium oxide, 9 wt.% free or uncombined ferric oxide and 2 wt.% zinc oxide.

The dry, modified ferrite-containing powder was then placed in a Patterson-Kelly blender and mixed with an aqueous solution containing 2 wt.% polyvinyl alcohol and 7 wt.% phosphoric acid to give a damp powder with a moisture content of approximately 28 wt.%. The damp ferrite powder was then pelletized (1/16-inch pellets) in a California pellet mill.

B. A total of 125 cc. of the pelleted catalyst compositon produced according to the procedure of Part A of this example was used to dehydrogenate butene-2 to butadiene-1,3 using a 25 mm. OD glass reactor approximately 13 inches long in the heated reactor section. Butene-2 was fed together with oxygen (as air) and steam over a fixed catalyst bed. The effluent gases from the reactor section were passed through a cold water condenser to removed most of the steam and samples of the effluent gas were withdrawn with a syringe at the exit from the condenser and were analyzed in a Perkin-Elmer vapor chromatograph. The butene-2 used was CP grade (99.0 mol percent minimim) and the oxygen was commercial grade purity (99.5 mol percent).

Prior to use, the catalyst composition was pretreated by reduction for 3 hours at 850°–1,050° F. in the presence of a fluent gas containing steam and a trickle of nitrogen. Steam was employed at a GHSV of approximately 12 times the GHSV at which the butene-2 was to be passed over the catalyst during the oxidative dehydrogenation. After the reduction step, butene-2 was fed to the reactor at an LHSV of 1.5 along with air and steam. Air was introduced to the reactor at a rate such that the oxygen/hydrocarbon mol ratio was 0.55/1 and steam was introduced at a steam/hydrocarbon mol ratio of 18/1. The conversion of butene-2 was 68.3 mol % and the selectively to butadiene-1,3 was 95.7 mol %. The overall yield of butadine-1,3 was 65.7 mol %.

EXAMPLE II

A zinc ferrite catalyst composition was prepared according to the method Examle IA except that no magnesium was present in the catalyst precursor mixture. The resulting catalyst compositon was pelletized (1/16 -inch pellets) and 125 cc. of the catalyst was reduced and employed to dehydrogenate butene-2 according to the method of Example IB. At an oxygen/hydrocarbon mol ratio of 0.55/1 and a steam hydrocarbon mol ratio of 20/1, the conversion of butene-2 was 65.8 mol % with a selectivity to butadiene-1,3 of 94.3 mol %. The overall yield of butadiene-1,3 was 62.0 mol %.

The above data demonstrate that the incorporation of magnesium into the zinc ferrite catalyst composition as shown in Example I provides a vastly superior catalyst composition. With the magnesium-modified catalyst, the conversion level of butene-2 was 2.5 mol % higher at a 1.4 mol % higher selectively and the yield was 3.7 mol % higher than for the unmodified zinc ferrite catalyst composition.

EXAMPLE III

To further illustrate the promotional effect of magnesium in the zinc ferrite catalyst compositons of this invention, two manganese-modified zinc ferrites were prepared with the following general composition: 86.2 g. ferric oxide (YLO 1788, C. Pfizer & Co.), 47.3 g. zinc carbonate, 3.0 g. zinc chloride and 7.85 g. manganese carbonate. In one catalyst composition, designated catalyst A, the zinc carbonate employed was that employed in the procedure of Example I (Naftone F-5637) and contained magnesium. The other catalyst composition, designated catalyst B, employed a zinc carbonate free from magnesium.

Catlysts A and B were prepared as follows: the above weights of materials were combined with 750 cc. of demineralized water in a 1-quart Waring Blender and blended for 20 minutes. The slurry was then poured into a Pyrex dish and dried overnight at 110° C. The dried cake was crushed and calcined at 1,125° F. for 15 minutes with air flow over the material during the calcination.

The calcined material was then coated onto a support material by placing 125 g. of 3–5 mesh AMC, 67.3 g. of the calcined ferrite composition, 2.47 g. of phosphoric acid (85%), and approximately 200 cc. of water in a laboratory pill coater. The coated catalysts were then pre-treated by reduction for 2 hours at 950° F. in the presence of a fluent gas consisting of steam and hydrogen. Steam was passed over the catalyst at a GHSV of 10 times the hydrocarbon feed rate to be employed and the hydrogen rate was 400 cc./min. The two catalysts were then employed to oxidatively dehydrogenate butene-2 at an LHSV of 1.5 in the presence of air and steam. The data from the experimental runs are recorded in the following table:

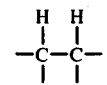

group at temperature of from about 500° to about 1,200° F. and in the presence of from about 0.2 to about 2.0 mols of oxygen per mol organic compound to thereby produce a dehydrogenated compound having the same number of carbon atoms in the presence of a catalyst composition consisting essentially of zinc ferrite having the empirical formula $Zn_xFe_yO_z$ wherein $x$ is from 0.1 to about 2, $y$ is about 0.3 to about 12, and $z$ is about 3 to about 18 and a promoter of magnesium oxide in an amount of from about 0.1 to about 10 wt.% and manganese oxide in an amount of about 0.1 to about 10 wt.% based on the weight of the zinc ferrite composition.

Table 1

| Catalyst | Hours on Stream | O₂/Steam/HC Mol Ratio | Conversion Mol % | Selectivity Mol % | Yield Mol % | Maximum Temp. ° C. |
|---|---|---|---|---|---|---|
| A | 435.25 | .56/15/1 | 74.8 | 95.4 | 71.3 | 900 |
| A | 700 | .61/15/1 | 77.4 | 94.6 | 73.2 | 912 |
| B | 336 | .50/20/1 | 66.7 | 95.5 | 63.7 | 922 |
| B | 737.75 | .56/15/1 | 71.1 | 94.6 | 67.3 | 886 |

The above data demonstrate that the incorporation of magnesium into the modified zinc ferrite catalyst composition results in a superior catalyst. With the magnesium-modified catalyst, the conversion level of butene-2 is from 6.3 to 8.1 mol % higher at comparable selectivities to produce a yield of from 5.9 to 7.6 mol % higher than for the zinc ferrite composition containing no magnesium.

From the foregoing description and Examples of this invention, those of ordinary skill in the art may make many modifications and variations therefrom without departing from the scope of the invention as hereinafter claimed.

We claim:
1. The process of oxidative dehydrogenation of organic compounds having from about 2 to about 20 carbon atoms and at least one

2. The process of claim 1 wherein the oxidative dehydrogenation is carried out in the additional presence of from about 2 to about 40 mols of diluent per mol of organic compound present, said diluent being selected from the group consisting of steam and nitrogen.

3. The process of claim 2 wherein the organic compound is selected from the group consisting of acyclic hydrocarbons having 4 to 5 contiguous non-quaternary carbon atoms, ethylbenzene and mixtures thereof.

4. The process of claim 2 wherein the organic compound is selected from the group consisting of butene-1, butene-2, the methylbutenes and mixtures thereof.

5. The process of claim 3 wherein the oxidative dehydrogenation is carried out in the additional presence of from about 0.0001 to about 1.0 mol of halogen per mol of organic compound present.

6. The process of claim 1 wherein the magnesium oxide promoter is present in the catalyst composition in an amount of from about 1.0 to about 5.0 wt.% based on the weight of the zinc ferrite catalyst composition.

7. The process according to claim 6 wherein manganese oxide is present in the catalyst composition in an amount of from about 1.0 to about 5.0 weight % based on the weigth of the zinc ferrite catalyst composition.

8. The process according to claim 1 wherein manganese oxide is present in the catalyst composition in an amount of from about 1.0 to about 5.0 weight % based on the weight of the zinc ferrite catalyst composition.

* * * * *